(12) United States Patent
Luce

(10) Patent No.: US 6,419,631 B1
(45) Date of Patent: Jul. 16, 2002

(54) NON-CONTACT TONOMETRY METHOD

(75) Inventor: David A. Luce, Clarence Center, NY (US)

(73) Assignee: Leica Microsystems Inc., Depew, NY (US)

( * ) Notice: Subject to any disclaimer, the term of this patent is extended or adjusted under 35 U.S.C. 154(b) by 0 days.

(21) Appl. No.: 09/553,111

(22) Filed: Apr. 20, 2000

(51) Int. Cl.$^7$ ................................. A61B 5/00
(52) U.S. Cl. ......................................... 600/401
(58) Field of Search ....................... 600/398, 399, 600/401, 405; 351/205, 208

(56) References Cited

U.S. PATENT DOCUMENTS

| | | | |
|---|---|---|---|
| 3,585,849 A | | 6/1971 | Grolman .................... 73/80 |
| 3,756,073 A | * | 9/1973 | Lavallee et al. ............ 600/401 |
| 5,279,300 A | * | 1/1994 | Miwa et al. ................ 600/401 |
| 5,779,633 A | * | 7/1998 | Luce ........................... 600/401 |

* cited by examiner

*Primary Examiner*—Max Hindenburg
(74) *Attorney, Agent, or Firm*—Hodgson Russ LLP

(57) ABSTRACT

During corneal deformation induced by a fluid pulse, observations associated with an inward first state of applanation and an outward second state of applanation are processed to provide a final reported intra-ocular pressure value that is substantially without error due to corneal thickness effects.

4 Claims, 5 Drawing Sheets

NON-CONTACT TONOMETRY METHOD

BACKGROUND OF THE INVENTION

A. Field of the Invention

The present invention relates to the field of ophthalmic instruments and methods, and more particularly to an improved method of non-contact tonometry for measuring intra-ocular pressure (IOP) of an eye.

B. Description of the Prior Art

Tonometers for measuring IOP were originally developed as "contact" type instruments, meaning that a portion of the instrument is brought into contact with the cornea during the measurement procedure. A well-known instrument of this type is the Goldmann applanation tonometer (GAT) originally developed during the 1950s. The GAT measures the force required to flatten ("applanate") a known area of the cornea, and is used today as a standard against which other types of tonometers are compared to assess measurement accuracy.

Patient discomfort caused by contact tonometers such as the GAT led to the development of "non-contact" tonometers (NCTs) which operate by directing an air pulse generated by a pump mechanism through a discharge tube aimed at the cornea to cause applanation. As the cornea is deformed by the fluid pulse, an opto-electronic system monitors the cornea by detecting corneally reflected light from a beam obliquely incident upon the cornea, and a peak detector signal occurs at the moment of applanation when the reflecting surface of the cornea is flat.

In state of the art NCTs, a pressure transducer measures the pump plenum pressure as the pulse is generated to provide a plenum pressure signal, which typically approximates a Gaussian distribution, whereby the plenum pressure at the moment applanation is achieved can be determined. The plenum pressure at applanation is then converted to an IOP value in units of mmHg using a linear regression equation stored during instrument clinical calibration relative to GAT as a reference. A primary index of an NCT's reliability is the standard deviation of differences $S_d$ of matched pairs of NCT and GAT clinical readings.

While NCTs provide reasonably reliable IOP measurements, recent studies indicate that corneal thickness effects can have a significant impact on NCT readings. IOP readings are falsely inflated because the air pulse expends some of its energy "bending" the corneal tissue itself, as opposed to displacing intra-ocular fluid pressing on the cornea. See, for example, Copt R-P, Thomas R, Mermoud A, *Corneal Thickness in Ocular Hypertension, Primary Open-angle Glaucoma, and Normal Tension Glaucoma*, Arch Ophthalmol. Vol. 117:14–16 (1999); Emara B, Probst L E, Tingey D P, Kennedy D W, et al., *Correlation of Intraocular Pressure and Central Corneal Thickness in Normal Myopic Eyes After Laser in situ Keratomileusis*, J Cataract Refract Surg, Vol. 24:1320–25 (1998); Stodtmeister R, *Applanation Tonometry and Correction According to Corneal Thickness*, Acta Ophthalmol Scand, Vol. 76:319–24 (1998); and Argus W A, *Ocular Hypertension and Central Corneal Thickness*, Ophthalmol, Vol. 102:1810–12 (1995). For persons with relatively thick corneas, IOP values measured under prior art methodology can be significantly effected. Heretofore, attempts to correct measured IOP for corneal thickness have typically involved measuring corneal thickness by additional instrument means and correcting measured IOP by an amount based upon the measured corneal thickness. U.S. Pat. No. 5,4740,66 (Grolman) issued Dec. 12, 1995 ascribes to this approach.

During a non-contact IOP measurement, the cornea is actually deformed from its original convex state through a first state of applanation to a slightly concave state, and is allowed to return from concavity through a second state of applanation to convexity as the air pulse decays. Indeed, a second peak is known to occur in the applanation signal corresponding to the second state of applanation. Heretofore, non-contact tonometry methods have only taken into account plenum pressure associated with the first state of applanation for inputting to a regression equation to calculate IOP, and have ignored plenum pressure associated with the second state of applanation.

SUMMARY OF THE INVENTION

It is therefore an object of the present invention to provide an improved non-contact tonometry method that provides a more accurate measurement of true IOP.

It is another object of the present invention to provide a non-contact tonometry method that eliminates corneal thickness as a factor effecting IOP measurement values.

It is a further object of the present invention to achieve the aforementioned objects using existing NCT hardware.

In view of these and other objects, a non-contact tonometry method according to a first embodiment of the present invention comprises the following steps. Initially, as in the prior art, a fluid pulse is directed at the cornea to cause reversible deformation of the cornea from convexity, through first applanation, to concavity, and back through second applanation to convexity. Corneal deformation is monitored as a function of time to generate a signal indicating times $t_1$ and $t_2$ of first applanation and second applanation, respectively. As corneal deformation is monitored, so to is a plenum pressure of the pump mechanism generating the fluid pulse in order to determine a first plenum pressure $PP_1$ and a second plenum pressure $PP_2$ corresponding to first and second applanation times $t_1$ and $t_2$, respectively. First plenum pressure $PP_1$ is input as a coefficient of a first regression equation to yield a first intra-ocular pressure value $IOP_1$, and second plenum pressure $PP_2$ is input as a coefficient of a second regression equation to yield a second intra-ocular pressure value $IOP_2$. The two values $IOP_1$ and $IOP_2$ are then averaged to compute a final reported intra-ocular pressure value $IOP_f$. Alternatively, an average $PP_{AVG}$ of the first and second plenum pressures could be input as a coefficient of a single corresponding regression equation to compute $IOP_f$.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

The improved method of tonometry according to the present invention can be implemented by an existing NCT having microprocessor control means, including NCTs manufactured by Leica Microsystems Inc., assignee of the present invention. As will be apparent to persons skilled in the art of ophthalmic instruments, implementation of the methods described herein is carried out by modifying the calibration technique and measurement control software of the instrument, and does not require different or additional hardware.

Figure 1:
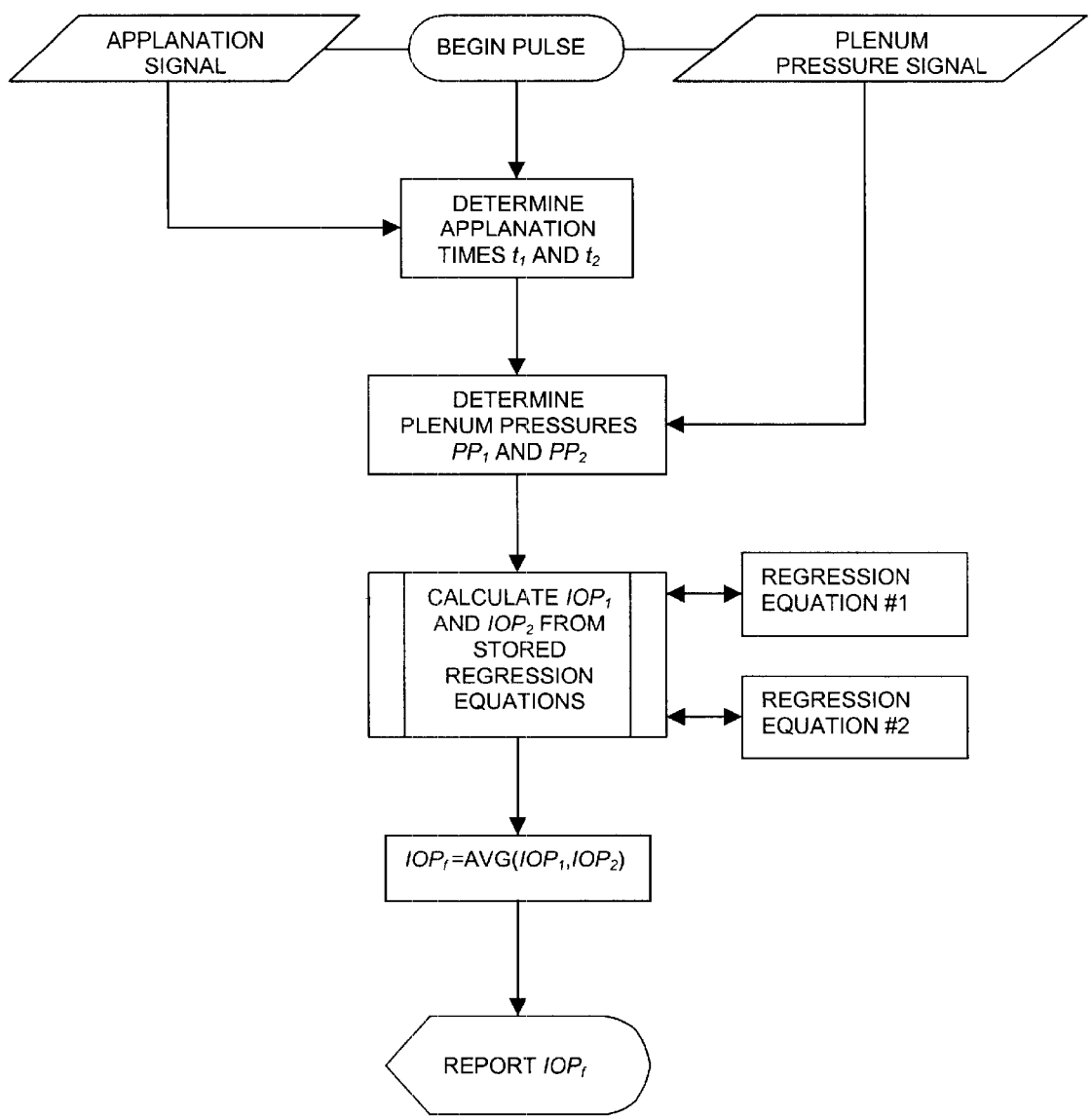
FIG. 1 is a schematic flowchart illustrating a non-contact tonometry method in accordance with one embodiment of the present invention.

As indicated in the flowchart of FIG. 1, NCT measurement begins with generation of a fluid pulse directed at the cornea. This is commonly accomplished by energizing a solenoid-driven pump mechanism in fluid communication with a fluid discharge tube aligned in front of the eye, as taught for instance in U.S. Pat. No. 3,756,073 incorporated herein by reference. The impulse energy imparted to the cornea by the fluid pulse reversibly deforms the cornea from its original state of convexity through a first state of applanation to a state of concavity. As the air pulse decays or is controllably diminished by de-energizing the pump solenoid, the cornea returns from concavity back through a second state of applanation to its original state of convexity. It is noted that use of a solenoid for driving the pump mechanism is common in the art, however alternative drive means such as linear motors are also known and could be employed.

Figure 2A:
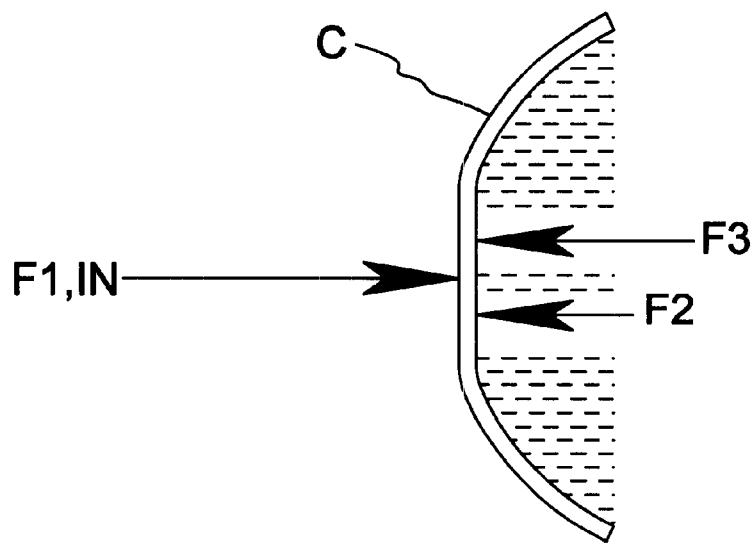
FIG. 2A is a force diagram of a cornea at a first moment of applanation.
Figure 2B:
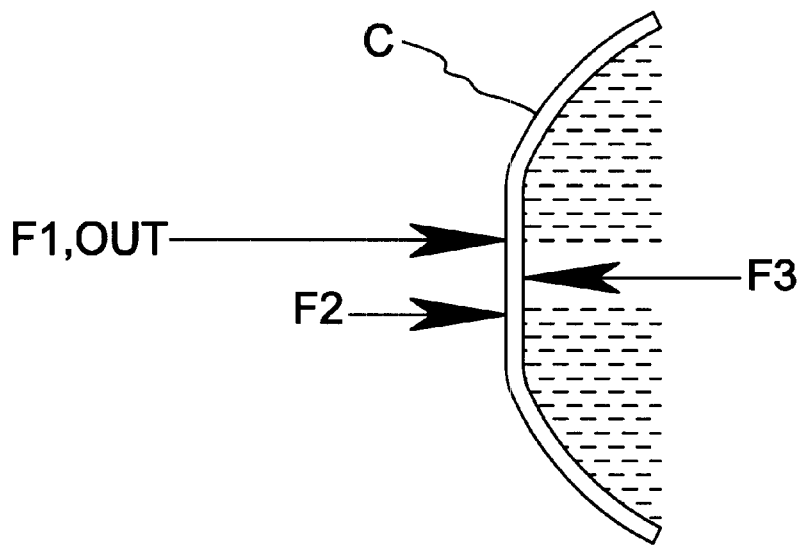
FIG. 2B is a force diagram of a cornea at a second moment of applanation.

FIGS. 2A and 2B are simplified diagrams showing the forces acting on a cornea C at the moment of first applanation (FIG. 2A) and second applanation (FIG. 2B) during an NCT measurement, while ignoring dynamic effects. In the figures, $F_1$ represents the inwardly directed force of an incident fluid pulse, $F_2$ represents the force required to bend the corneal tissue itself, and $F_3$ represents the outwardly directed force attributed to intra-ocular pressure, the quantity to be measured. At first applanation, the force $F_2$ is acting in concert with force $F_3$ to counter the force $F_1$ exerted by the fluid pulse:

$$F_{1,OUT} + F_2 = F_3$$

However, at second applanation the force $F_2$ is acting together with fluid pulse force $F_1$ to oppose the force $F_3$ exerted by intra-ocular pressure:

$$F_{1,OUT} + F_2 = F_3$$

Therefore, the system can be expressed by the following relationship:

$$F_3 = \frac{F_{1,IN} + F_{1,OUT}}{2}$$

In the above equation, it is notable that the force $F_2$ due to corneal thickness has "dropped out" such that $F_3$ is expressed purely in terms of $F_{1,IN}$ and $F_{1,OUT}$. Since $F_{1,IN}$ and $F_{1,OUT}$ are directly related to an observable quantity, namely the pump plenum pressure, and true IOP is directly related to $F_3$, the sought after true IOP can be measured without corneal thickness effects by using data from both the first and second states of applanation as described below. This approach, wherein the second state of applanation is taken into consideration in measuring IOP, is a departure from prior art methods.

Figure 3:
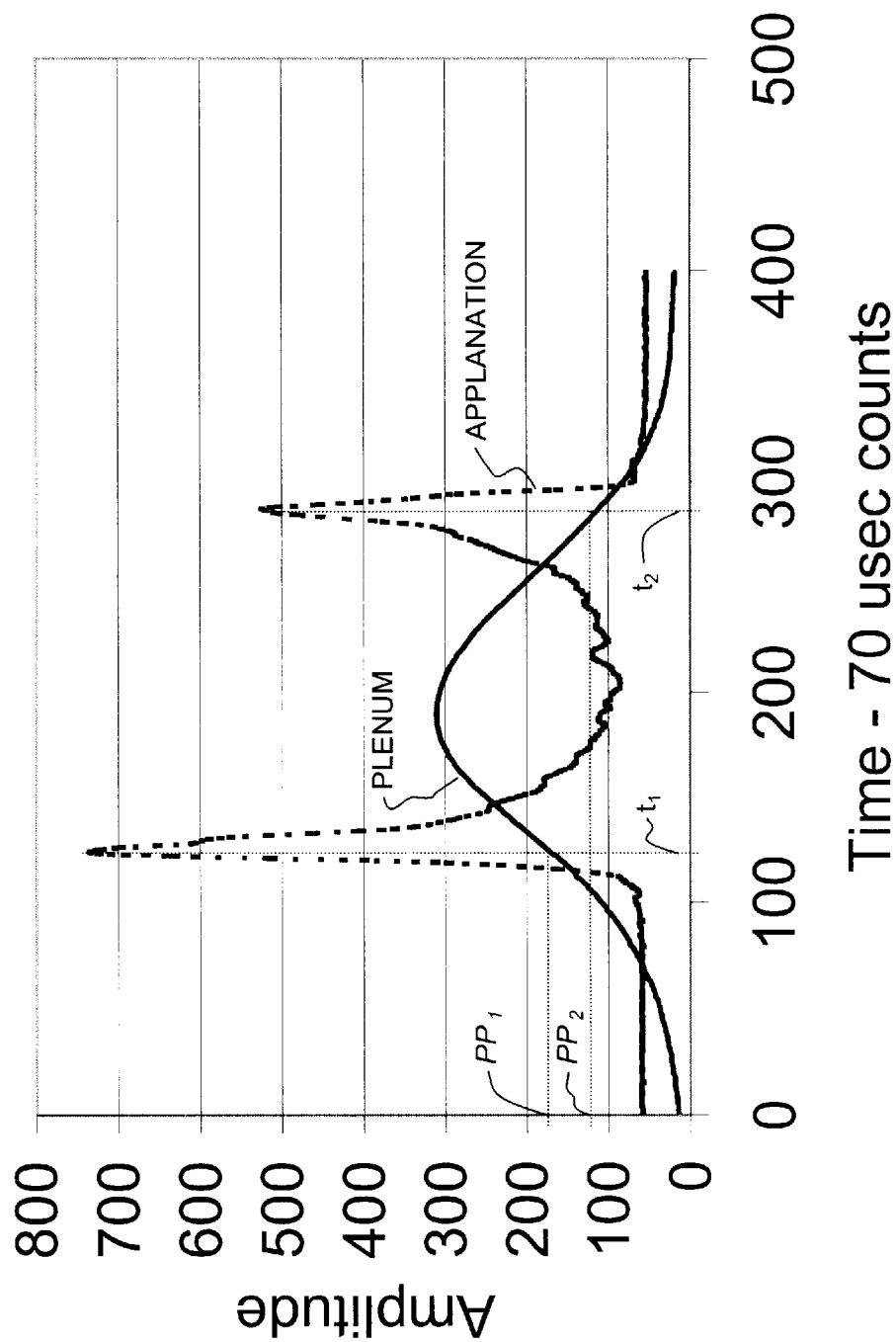
FIG. 3 is a graph showing applanation detection and plenum pressure signals for a typical NCT IOP measurement.
Figure 4:
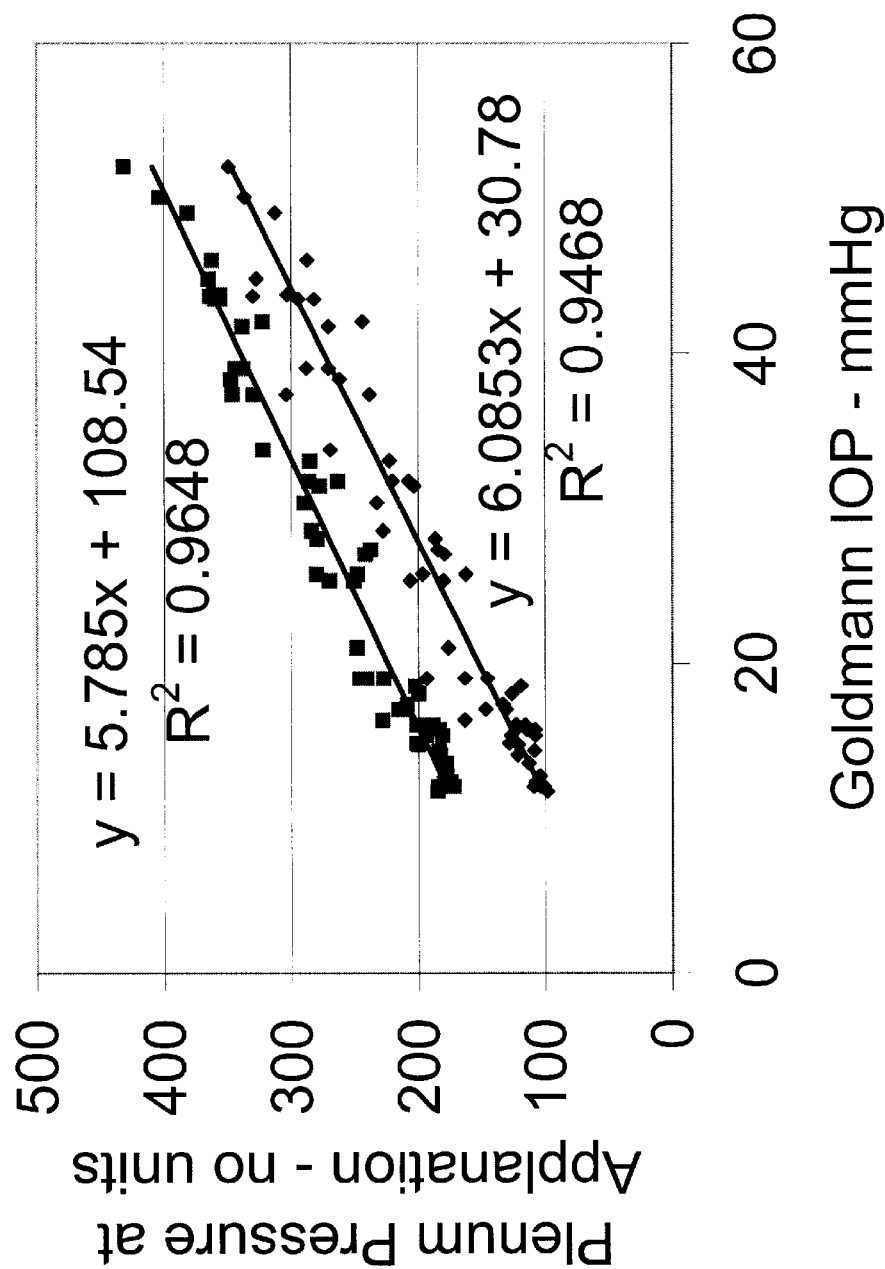
FIG. 4 is a graph showing linear regressions of plenum pressures for both inward (first) and outward (second) applanation plenum pressures.

Attention is now confined to FIGS. 1, 3, and 4 for description of a preferred tonometry method according to the present invention. During the corneal deformation described above, an opto-electronic system of the NCT monitors the shape of the cornea and provides an applanation signal. More specifically, as is known in the art, an infra-red emitter is positioned on one side of a central alignment axis of the instrument to direct an obliquely incident beam of light to the cornea, and a light-sensitive detector is positioned on the other side of the alignment axis symmetrically opposite the emitter for receiving corneally reflected light. When the cornea is convex or concave, the obliquely incident beam is fanned out as it reflects from the curved corneal surface, and most of the reflected light misses the detector. However, as the cornea approaches a state of applanation, the obliquely incident beam is reflected in a coherent manner from the flat corneal surface toward the detector. Consequently, the detector generates a peak signal indicating applanation. FIG. 3 shows an actual applanation signal over time, with a first peak indicating a first time of applanation $t_1$ and a second peak indicating a second time of applanation $t_2$. Pursuant to FIG. 1, the applanation signal information is input to processing means for determining first and second applanation times $t_1$ and $t_2$. Under prior art methods, only the first applanation time $t_1$ was registered. Also during corneal deformation, a plenum pressure associated with the pump mechanism is measured as a function of time to provide a plenum pressure signal. Plenum pressure can be measured directly by a miniature pressure transducer, or indirectly by correlating pressure and time for a pressure ramp increasing at a known rate, both of these approaches being known in the art of non-contact tonometry. FIG. 3 shows an actual plenum pressure signal superimposed on the applanation signal. The plenum pressure signal typically approximates a Gaussian distribution. The plenum pressure signal, like the applanation signal, is input to processing means, thus enabling determination of a first plenum pressure $PP_1$ at first applanation time $t_1$ and a second plenum pressure $PP_2$ at second applanation time $t_2$.

In accordance with the method of the described embodiment, both plenum pressures $PP_1$ and $PP_2$ are input to respective regression equations stored in instrument memory as a result of instrument calibration in a clinical setting. FIG. 4 presents an example of a plot of clinical calibration measurements used to formulate two respective linear regression equations for a non-contact tonometer incorporating methodology of the present invention. Each eye studied in the clinical trial is measured by GAT and NCT instruments. The diamond shaped data points represent first plenum pressure $PP_1$ as measured by the NCT (y-axis) against the corresponding GAT measurement in mmHg (x-axis), while the square shaped data points likewise represent second plenum pressure $PP_2$ as measured by the NCT against the corresponding GAT measurement. The two sets of calibration data points are fitted to respective regression equations, such as linear regression equations determined by a least squares algorithm, and the regression equations are stored in the instrument memory. It is noted that while linear regression equations are shown herein in connection with FIG. 4, non-linear regression equations may also be derived and would fall under the methodology of the present invention.

During an actual patient measurement according to the described embodiment, first plenum pressure $PP_1$ is converted to a first intra-ocular pressure value $IOP_1$ using the first regression equation, and second plenum pressure $PP_2$ is converted to a second intra-ocular pressure value $IOP_2$ using the second regression equation. The first and second IOP values are then averaged as suggested by the discussion of FIGS. 2A and 2B such that corneal thickness effects cancel out. The averaging step yields a final reported value $IOP_f$.

Figure 5:
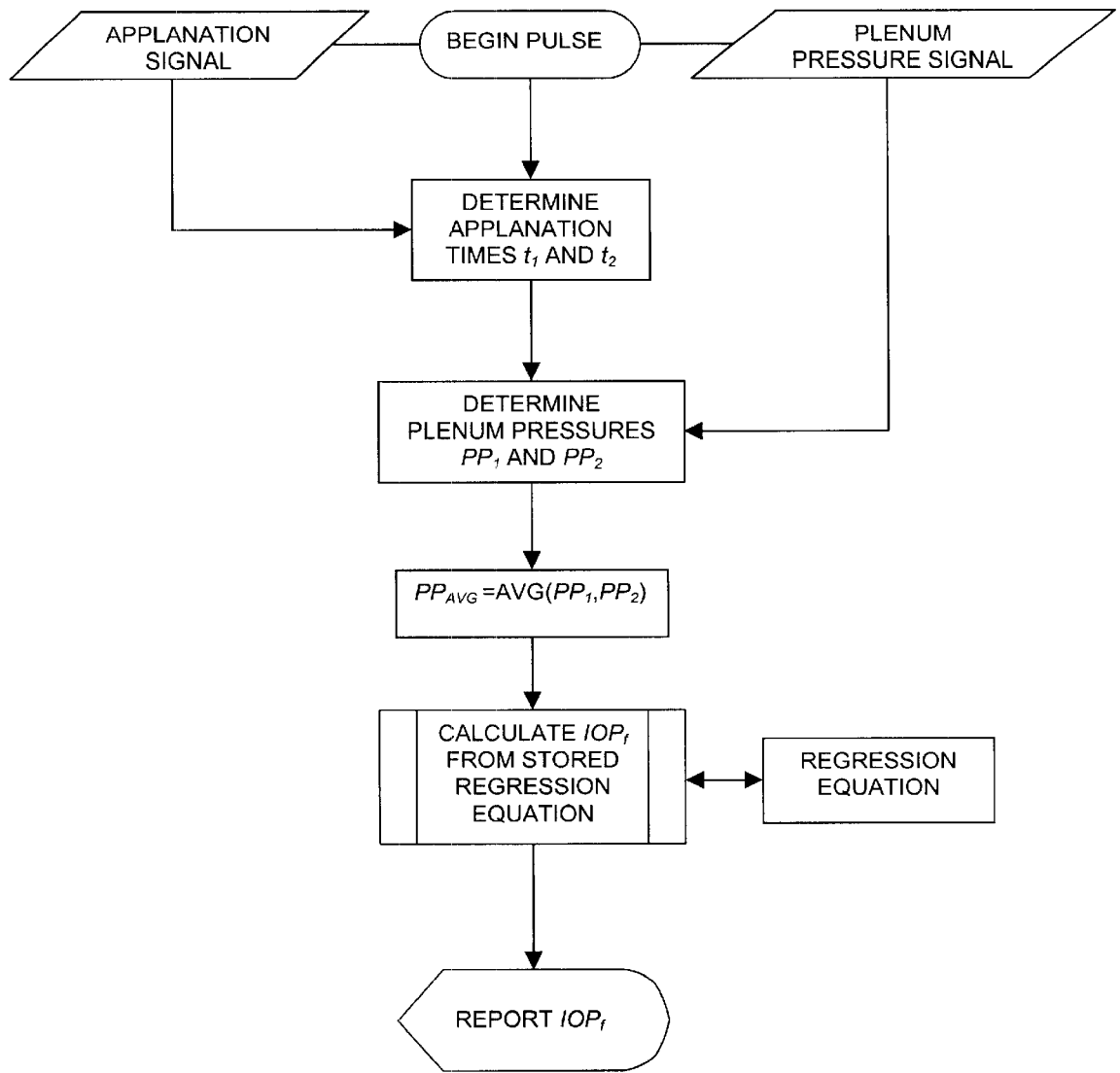
FIG. 5 is a schematic flowchart illustrating a non-contact tonometry method in accordance with another embodiment of the present invention.

As an alternative to the approach described above, the first and second plenum pressures $PP_1$ and $PP_2$ can be averaged to yield $PP_{AVG}$, and this average value can be input to a single regression equation determined by clinical calibration for the instrument to yield the final reported value $IOP_f$. This approach is shown schematically in FIG. 5. In contrast to the above-mentioned calibration method in which first and second NCT plenum pressures $PP_1$ and $PP_2$ are each plotted separately against corresponding GAT measurements to determine two respective regression equations, calibration under the alternative approach would involve averaging the NCT plenum pressures $PP_1$ and $PP_2$ and plotting the average against the corresponding GAT measurement. This set of calibration data points is fitted to a single regression equation, such as a linear regression equation determined by a least squares algorithm, and the single regression equation is stored in the instrument memory.

What is claimed is:

1. A method of measuring intra-ocular pressure of an eye comprising the steps of:

(A) directing a fluid pulse at a cornea to cause reversible deformation of said cornea from an original state of convexity through a first state of applanation to a state of concavity, and back through a second state of applanation to said state of convexity;

(B) monitoring said corneal deformation as a function of time to generate a signal indicating a time of said first state of applanation and a time of said second state of applanation;

(C) measuring a first plenum pressure corresponding to said time of said first state of applanation and a second plenum pressure corresponding to said time of said second state of applanation;

(D) inputting said first and second plenum pressures to respective first and second regression equations to provide respective first and second intra-ocular pressure values; and (E) calculating a final intra-ocular pressure value based on said first and second intra-ocular pressure values.

2. The method of measuring intra-ocular pressure according to claim 1, wherein said final intra-ocular pressure value is calculated by averaging said first and second intra-ocular pressure values.

3. A method of measuring intra-ocular pressure of an eye comprising the steps of:

(A) directing a fluid pulse at a cornea to cause reversible deformation of said cornea from an original state of convexity through a first state of applanation to a state of concavity, and back through a second state of applanation to said state of convexity;

(B) acquiring pressure data associated with said fluid pulse at a time of said first state of applanation and at a time of said second state of applanation; and (C) calculating a final intra-ocular pressure value based on said acquired pressure data.

4. A method of measuring intra-ocular pressure of an eye comprising the steps of:

(A) directing a fluid pulse at a cornea to cause reversible deformation of said cornea from an original state of convexity through a first state of applanation to a state of concavity, and back through a second state of applanation to said state of convexity;

(B) monitoring said corneal deformation as a function of time to generate a signal indicating a time of said first state of applanation and a time of said second state of applanation;

(C) measuring a first plenum pressure corresponding to said time of said first state of applanation and a second plenum pressure corresponding to said time of said second state of applanation;

(D) averaging said first plenum pressure and said second plenum pressure to provide an average plenum pressure; and (E) inputting said average plenum pressure to a corresponding regression equation to calculate a final intra-ocular pressure value.

* * * * *